United States Patent [19]

Scribner

[11] Patent Number: 5,395,353
[45] Date of Patent: Mar. 7, 1995

[54] GUIDING CATHETER WITH CONTROLLABLE PERFUSION PORTS

[75] Inventor: Robert M. Scribner, Boulder, Colo.

[73] Assignee: Vascular Technologies, Inc., Boulder, Colo.

[21] Appl. No.: 146,616

[22] Filed: Nov. 2, 1993

[51] Int. Cl.6 ............................................. A61M 5/00
[52] U.S. Cl. .................... 604/264; 604/248; 604/256
[58] Field of Search ............... 604/264, 248, 249, 27, 604/28, 43, 4, 256, 280, 49

[56] References Cited

U.S. PATENT DOCUMENTS

| | | | |
|---|---|---|---|
| 1,566,061 | 12/1925 | Ziegler . | |
| 3,030,953 | 4/1962 | Koehn . | |
| 4,129,129 | 12/1978 | Amrine | 604/43 X |
| 4,129,129 | 12/1978 | Amrine . | |
| 4,184,497 | 1/1980 | Kolff et al. | 131/213 A |
| 4,204,328 | 5/1980 | Kutner | 433/29 |
| 4,248,224 | 2/1981 | Jones | 128/214 R |
| 4,301,797 | 11/1981 | Pollack . | |
| 4,639,252 | 1/1987 | Kelly et al. | 604/282 |
| 4,643,712 | 2/1987 | Kulik et al. | 604/4 |
| 4,666,426 | 5/1987 | Aigner | 604/5 |
| 4,787,882 | 11/1988 | Claren | 604/256 X |
| 4,850,969 | 7/1989 | Jackson | 604/96 |
| 5,158,553 | 10/1992 | Berry et al. | 604/248 |
| 5,163,921 | 11/1992 | Feiring | 604/247 |
| 5,195,971 | 3/1993 | Sirhan | 604/96 |

*Primary Examiner*—John D. Yasko
*Attorney, Agent, or Firm*—Sheridan Ross & McIntosh

[57] ABSTRACT

A guiding catheter capable of selective blood perfusion, position detecting, and enhanced contrast media injection. The catheter generally comprises an elongated tubular member for guiding contrast media or medical instruments into a selected blood vessel. The tubular member includes at least one perfusion port in a sidewall thereof for allowing passive blood perfusion of the blood vessel while the catheter is seated in a vascular ostium. The catheter further comprises a closure member positioned adjacent the perfusion port and movable between at least first and second positions to open and at least partially close the perfusion port. An actuating member is operatively connected to the closure member and extends proximally therefrom toward a proximal end of the tubular member, whereby the actuating member is selectably moveable to move the closure member between the first and second positions.

43 Claims, 4 Drawing Sheets

FIG. 5

GUIDING CATHETER WITH CONTROLLABLE PERFUSION PORTS

FIELD OF THE INVENTION

The present invention relates to medical devices for providing access to the vascular system and, more particularly, to a guiding catheter having perfusion ports which are closable to provide the ability to selectively perfuse a blood vessel and to enhance positioning ability by, e.g., detecting blood pressure damping in the catheter lumen or improving contrast media injection.

BACKGROUND OF THE INVENTION

In the performance of vascular intervention procedures, guiding catheters are routinely used to guide medical instruments and/or radiopaque contrast media into a selected blood vessel. For example, guiding catheters can be used to guide balloon-tip catheters (i.e., for coronary angioplasty procedures) and atherectomy instruments (i.e., for coronary atherectomy procedures) through the femoral artery of a patient for access to the coronary arteries via the ascending and descending aorta.

Guiding catheters typically comprise an elongated, torque-transmitting, tubular member open at both ends and having perfusion ports in a sidewall thereof. Such perfusion ports are usually located within about 3 centimeters of the distal tip such that, when the distal tip is seated in, for example, an ostium of a coronary artery, blood can enter the perfusion ports from the aorta and pass through the lumen of the guiding catheter and out the distal tip to perfuse the selected coronary artery.

Proper positioning of a guiding catheter in the selected coronary artery is an important aspect of successful coronary interventions. Briefly, this involves inserting the guiding catheter into the femoral artery, feeding the guiding catheter into the ascending aorta, and seating the distal tip in the appropriate coronary ostium. Insertion of a guiding catheter into a femoral artery can be accomplished by a standard percutaneous catheter introduction technique, such as by the use of a catheter introducer which is inserted into the femoral artery using the Seldinger technique. Feeding the guiding catheter into the ascending aorta typically involves passing (e.g., over a guidewire) a sufficient length (e.g., about 80 cm) of the catheter into the femoral artery until the distal tip completes its travel up the descending aorta and down the ascending aorta. In order to properly seat the distal tip of the guiding catheter into the selected coronary ostium, the physician typically repeatedly injects radiopaque contrast media and, by viewing the contrast media flow on an x-ray monitor (e.g., a fluoroscope) while manipulating the catheter distal tip, gradually seats the distal tip.

When seating the distal tip in the selected coronary ostium, it can be appreciated that it would be beneficial to have the ability to sense (i.e., by the physician, at the proximal end of the tubular member) when the distal tip is improperly seated against the aortic wall (e.g., when the distal tip is at least partially obstructed by the aortic wall). In many instances, this would significantly reduce the number of contrast media injections needed to properly seat the catheter, thereby saving time and contrast media. When seating catheters without perfusion ports, such sensing can be accomplished by sensing the damping of the blood pressure wave in the lumen of the guiding catheter which would accompany the blocking of the distal tip (e.g., by sensing pressure fluctuations in the lumen utilizing a pressure sensor at the proximal end of the catheter). However, when using known catheters with perfusion ports, the damping of the blood pressure wave generally does not occur because the perfusion ports remain open when the distal tip is seated against the aortic wall.

Once the distal tip has been properly seated in the selected coronary ostium, contrast media is typically injected through the lumen of the catheter and into the artery so that the position of the obstruction (e.g., atherosclerosis) within the selected coronary artery can be viewed on an x-ray monitor. Further, once the intervention procedure has been performed, contrast media can be injected to assess the results of the intervention. With many known devices, the presence of perfusion ports impairs the ability to effectively inject high concentrations of contrast media into the artery because a portion of the contrast media can exit the guiding catheter lumen through the perfusion ports and can be dispersed with blood flow in the ascending aorta. It can be appreciated that such dispersal with aortic blood can significantly increase the amount of contrast media required for adequate visualization of the selected artery. In this regard, dispersal of large amounts of contrast media can result in disruption of kidney functions or cause other complications.

SUMMARY OF THE INVENTION

Accordingly, it is an object of the present invention to provide an improved guiding catheter having vascular perfusion and enhanced seating capabilities. It is a related object to provide a guiding catheter wherein blood pressure waves within the catheter lumen will be damped upon improper seating of the distal tip against a vascular wall.

It is another object of the present invention to provide an improved guiding catheter wherein the ability to efficiently supply contrast media to a blood vessel is enhanced. It is a related object to provide a guiding catheter wherein injected contrast media can be selectively inhibited from exiting through perfusion ports in the catheter.

The present invention is embodied in an assembly particularly adapted to facilitate selective vascular perfusion while also providing improved contrast media injection and detection of blood pressure damping caused by improper seating of the distal tip. Such functional objects are achieved through the provision of a guiding catheter having perfusion ports which are selectively controllable between open and closed conditions.

The assembly includes an elongated tubular member open at both a proximal end and a distal tip and including at least one perfusion port, and preferably two perfusion ports, in a sidewall thereof (e.g., positioned on opposing sides of the tubular member, approximately 180° from each other). A closure member is positioned adjacent to the perfusion port and is movable relative to the perfusion port between a first position, wherein the perfusion port is open, and a second position, wherein the perfusion port is at least partially, and preferably completely, closed. Preferably, the closure member is biased (e.g., by its own elasticity or other suitable means) toward the first position. Such biasing obviates the need to maintain the closure member in the first position, thereby freeing the user's hands to perform other needed operations.

An actuating member is operatively connected to the closure member and extends proximally therefrom toward the proximal end of the tubular member. The actuating member provides a means whereby the user of the catheter can selectively move the closure member between the first position and the second position to thereby selectively open and close the perfusion port.

Movement of the closure member relative to the perfusion port can comprise any of a number of movements. For example, such movement can be rotational whereby the closure member is rotated relative to the tubular member (i.e., relative to the perfusion port). Alternatively, the movement can be axial (i.e., proximally/distally in the direction of the longitudinal extent of the tubular member) whereby the closure member is pushed or pulled axially relative to the tubular member. If desired, the movement can also be a combination of rotational and axial movements.

In one embodiment, the closure member includes a cylindrical member positioned adjacent to, and preferably about (i.e., around the exterior of), the tubular member. The cylindrical member has a perfusion hole, and preferably two perfusion holes, through a sidewall thereof which is in alignment with the perfusion port when the closure member is in the first position and is misaligned with the perfusion port when the closure member is in the second position. When the perfusion hole is aligned with the perfusion port (i.e., when the closure member is in the first position), the catheter will allow passive flow of fluid (e.g., blood) into the perfusion ports and through the lumen of the tubular member to perfuse the selected blood vessel. Operative connection between the closure member (i.e., the cylindrical member) and the actuating member can be provided by securement (e.g., by adhesive) of the proximal end of the cylindrical member to the distal end of the actuating member. As such, movement of the closure member (i.e., the cylindrical member) from the first position to the second position can be accomplished by movement of the actuating member.

Preferably, the movement of the closure member comprises a rotation of the proximal end of the cylindrical member relative to the distal end of the cylindrical member to thereby twist the cylindrical member. In this regard, the cylindrical member is preferably made from an elastomeric material. The distal end of the cylindrical member may be secured (e.g., by adhesive) to the tubular member at a location distal to the perfusion port, such that the cylindrical member may be twisted by rotating the actuating member (secured to the proximal end of the cylindrical member) relative to the tubular member (secured to the distal end of the cylindrical member). Preferably, such rotation of the actuating member is accompanied by an axial movement of the actuating member relative to the tubular member, corresponding with axial contraction of the cylindrical member due to the twisting thereof.

The actuating member may include a cylindrically-shaped sleeve member slidably positioned adjacent to, and preferably positioned about, the tubular member. As noted above, such sleeve member may extend in a proximal direction from the proximal end of the cylindrical member to a location near the proximal end of the tubular member. A hemostasis valve may further be provided within a hub on the proximal end of the sleeve member for providing a seal between the sleeve member and the tubular member.

In one embodiment, the tubular member includes a proximal portion, having a proximal outer diameter, and a distal portion, having a distal outer diameter larger than the proximal outer diameter. The perfusion port is preferably positioned in the proximal portion of the tubular member and, accordingly, the cylindrical member and sleeve member are positioned about the proximal portion. Such reduced diameter of the proximal portion assists in maintaining the maximum diameter of the assembly below a predetermined value, even though the sleeve member and cylindrical member are positioned about the tubular member.

In order to ensure optimum closure of the perfusion ports, the assembly may further include means for limiting movement of the actuating member relative to the tubular member. In one embodiment, such means for limiting movement includes threads on the interior of a hub attached to the sleeve member mating with threads on the exterior of a hub attached to the tubular member. The mating threads may further include a discontinuity (e.g., an end to the threads or a stop member) whereby the rotational and axial movement of the sleeve member relative to the tubular member is limited.

In use, the guiding catheter is introduced into a blood vessel (e.g., the aorta) and advanced toward the selected vascular ostium (e.g., a coronary artery ostium). The position of the distal tip relative to the vascular ostium is then detected while the perfusion port is at least partially, and preferably completely, closed. Subsequently, the blood vessel is selectively perfused to provide adequate blood supply thereto. Information from the detection step may then be utilized to position (e.g., by advancing, withdrawing, or rotating) the distal tip relative to the vascular ostium. Preferably, such steps of detecting a position of the distal tip and positioning the distal tip are iteratively performed until the distal tip is properly seated in the selected vascular ostium.

The step of selectively perfusing the blood vessel may comprise opening the perfusion port by, for example, selectively moving (e.g., rotating or axially displacing) the closure member relative to the perfusion port. Preferably, the closure member is moved by securing the tubular member relative to the blood vessel and moving the actuating member relative to the tubular member to move the closure member from the second position to the first position. More preferably, the step of opening the perfusion port comprises both rotational and axial movements of the actuating member relative to the tubular member.

In one embodiment, the perfusion port is biased toward the open condition. As such, in order to detect the position of the distal tip while the perfusion port is at least partially closed, the method can further include the step of selectively at least partially, and preferably completely, closing the perfusion port before the detecting step. Such step can be performed by selectively moving (e.g., rotating or axially displacing) the closure member relative to the perfusion port, similar to the step of opening the perfusion port.

The step of detecting the position of the distal tip relative to the selected vascular ostium may comprise sensing a blood pressure wave in the tubular member utilizing, for example, pressure sensors located at the proximal end of the tubular member. Such sensing allows detection of a blood pressure wave damping which may occur when the distal tip is improperly seated against a vascular wall. The step of detecting the position of the distal tip may also comprise injecting contrast media through the tubular member (i.e., with the perfusion port closed) and viewing the position of the distal tip relative to the selected vascular ostium on an x-ray monitor.

A method is further provided for using the above-described guiding catheter to visualize the internal lumen of a blood vessel. Such method generally comprises the steps of seating the distal tip in the selected vascular ostium, introducing contrast media into the tubular member with the perfusion port at least partially closed, and selectively perfusing the selected blood vessel in order to alleviate patient discomfort associated with insufficient blood supply to the blood vessel. Selective perfusion may be performed by selectively opening the perfusion port to allow blood to enter the tubular member through the perfusion ports and exit the tubular member through the distal tip to perfuse the selected blood vessel.

The step of selectively opening the perfusion port may comprise selectively moving (e.g., rotating or axially displacing) the closure member relative to the perfusion port. Preferably, the closure member is moved by securing the tubular member relative to the blood vessel and moving the actuating member relative to the tubular member to move the closure member from the second position to the first position. More preferably, the step of selectively opening the perfusion port comprises both rotational and axial movements of the actuating member relative to the tubular member.

As noted above, in one embodiment, the perfusion port is biased toward the open condition. As such, in order to introduce contrast media into the guiding catheter while the perfusion port is at least partially closed, the method can further include the step of selectively at least partially, and preferably completely, closing the perfusion port to inhibit blood flow through the guiding catheter before the injecting step. Such step can be performed by selectively moving (e.g., rotating or axially displacing) the closure member relative to the perfusion port, similar to the step of opening the perfusion port. The steps of selectively perfusing the blood vessel (e.g., by opening the perfusion port) and selectively closing the perfusion port may be successively performed to allow enhanced blood vessel visualization while providing sufficient blood supply (i.e., perfusion) to the selected blood vessel.

BRIEF DESCRIPTION OF THE DRAWINGS

FIG. 2b is the guiding catheter of FIG. 2a with the perfusion ports in the closed condition;

FIG. 3 is a section view of the perfusion ports and perfusion holes taken along line 3—3 in FIG. 2a.

DETAILED DESCRIPTION

The Figures illustrate a guiding catheter 30 embodying the features of the present invention. Although this embodiment of the present invention will be described with reference to a guiding catheter for use in coronary artery intervention procedures, it should be appreciated that the present invention is also applicable to other vascular intervention devices wherein catheters with perfusion ports are utilized. For example, the present invention could be used for venous interventions or any other procedure where perfusion of a blood vessel is required.

For ease of description, in the discussion of the catheter 30, the term "distal" refers to the direction toward the patient 10 (i.e., toward the distal tip 46 of the catheter 30 following the path of the tubular member). Correspondingly, the term "proximal" refers to the direction away from the patient 10 (i.e., toward the proximal end 44 of the catheter 30 following the path of the tubular member).

Figure 1:
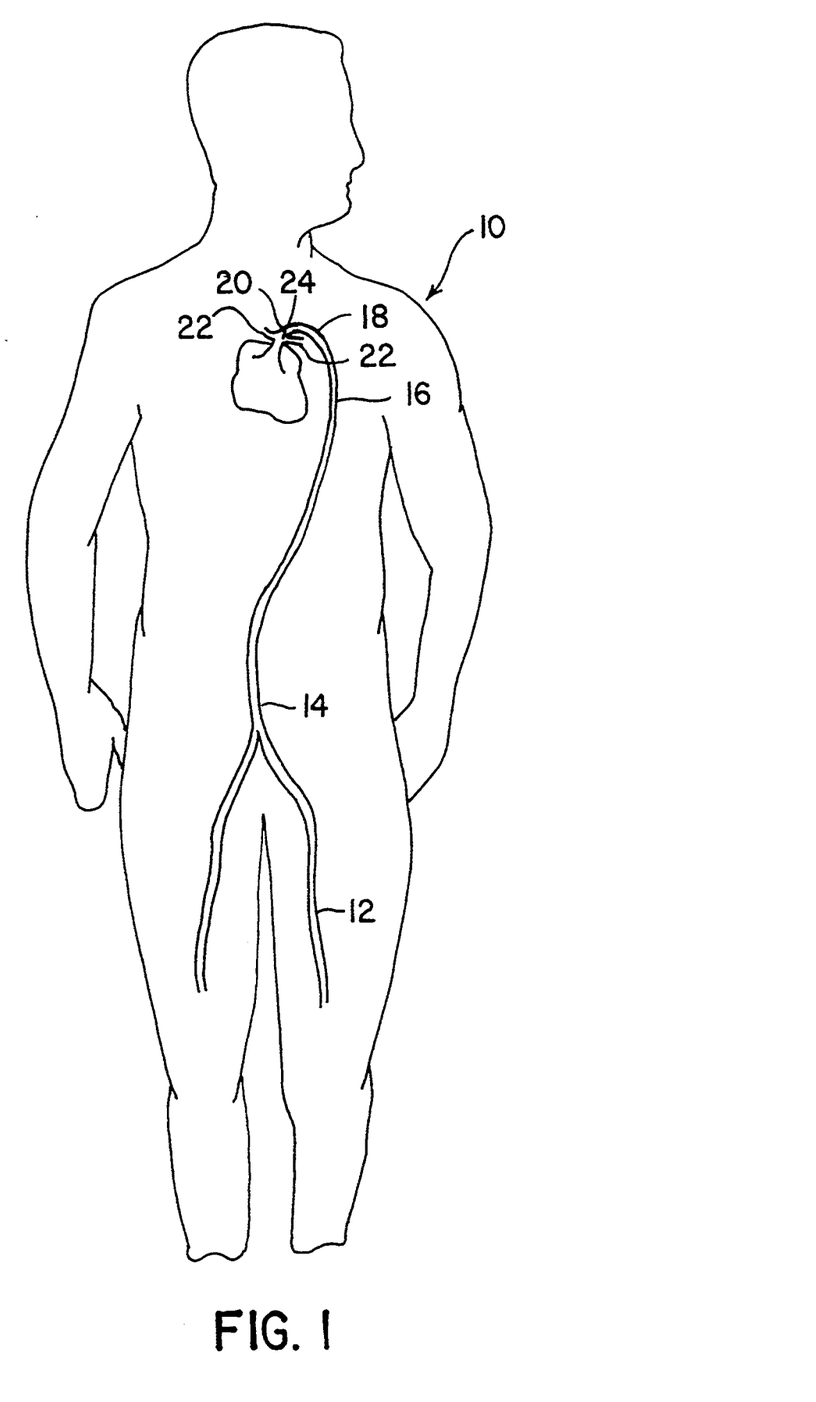
FIG. 1 is a front view of a patient showing the heart, ascending aorta, aortic arch, descending aorta, abdominal aorta, and femoral artery.

FIG. 1 shows the path through which a guiding catheter 30 will be inserted for a coronary artery intervention. Briefly, the guiding catheter 30 will be inserted into the femoral artery 12 (e.g., utilizing a catheter introducer, not shown), through the abdominal aorta 14, up the descending aorta 16, through the aortic arch 18, and down the ascending aorta 20 until the distal tip 46 of the guiding catheter 30 is near the selected coronary artery 22. The distal tip 46 can subsequently be seated in a selected coronary ostium 24 and the required procedure (e.g., angiography, angioplasty, atherectomy, etc.) can be performed.

Figure 2A:
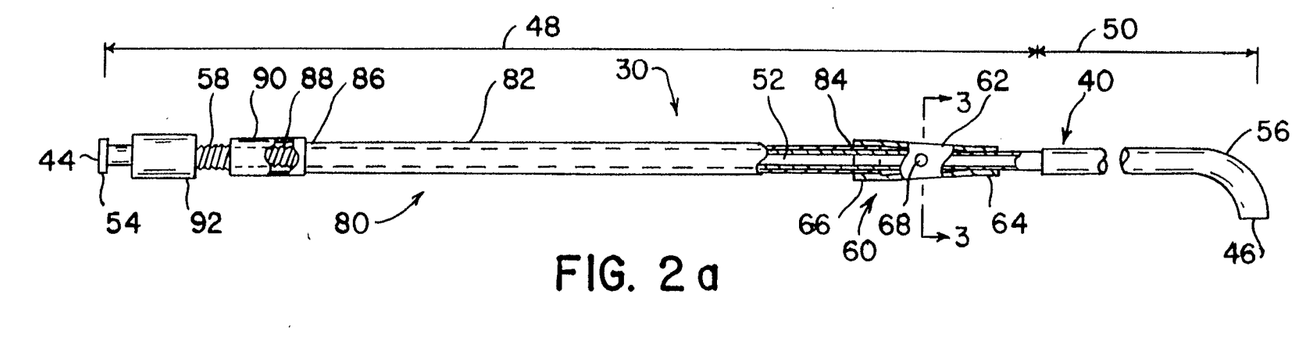
FIG. 2a is a side view of a guiding catheter embodying the present invention with the perfusion ports in the open condition.

FIG. 2a illustrates a guiding catheter 30 embodying the features of the present invention. The catheter 30 generally comprises an elongated tubular member 40 having perfusion ports 42 in a sidewall thereof and means for selectively closing the perfusion ports 42 in the tubular member 40. In the present embodiment, the means for selectively closing the perfusion ports 42 includes a closure member 60 and an actuating member 80 operatively connected to the closure member 60 and extending proximally therefrom toward a proximal end 44 of the tubular member 40.

The tubular member 40 of the present embodiment is an elongated, cylindrically-shaped member open at both a proximal end 44 and a distal tip 46. When used as a guiding catheter for coronary artery interventions, the tubular member 40 should have a length sufficient to travel from an incision in the femoral artery 12 to the selected coronary ostium 24. In the present embodiment, such length is about 100 cm. The inner diameter of the tubular member 40 must be of sufficient size to enable the introduction of an appropriate medical instrument (e.g., contrast media, balloon catheter or atherectomy instrument) through the tubular member 40 and into the appropriate coronary artery 22. For example, inner diameters of guiding catheters are typically in the range of 0.070 inches to 0.107 inches and, for femoral artery applications, are preferably at least about 0.080 inches.

The tubular member 40 can be divided into a proximal portion 48 (e.g., proximal 75 cm) and a distal portion 50 (e.g., distal 25 cm), defined by their different outer diameters. In the described embodiment, the distal portion 50 has an outer diameter equal to that of a standard 9 French guiding catheter (i.e., about 0.117 inches). The proximal portion 48, on the other hand, has a reduced diameter to accommodate the positioning of the closure member 60 and actuating member 80 around the circumference of the tubular member 40 without dramatically increasing the overall diameter of the catheter beyond the standard size (e.g., about 0.117 inches). In this regard, the outer diameter of the proximal portion 48 of the tubular member 40 is about 0.106 inches.

In the present embodiment, the tubular member 40 is produced by modifying (e.g., by centerless grinding) a standard three-layer, 9 French guiding catheter. The inner layer of the standard catheter is a low-friction polymer material, such as polytetrafluoroethylene, for providing a smooth surface to slide medical instruments through the lumen 52 of the guiding catheter 30. The middle layer is a tubular braided support material, such as metallic, polymeric or aramid fiber (e.g., Kevlar) braid for providing torque transmission over the length of the guiding catheter. The outer layer is a low-friction polymer material, such as polyurethane, for allowing smooth insertion of the guiding catheter into an artery and retention of anatomic curve shapes. A commercially available product, such as a Schneider 9F Superflow Guide Catheter having an external diameter of about 0.117 inches, could be used for the tubular member 40 with the following modification. The proximal portion 48 (e.g., about 75 cm long) is centerless ground to reduce the outside diameter of the tubular member 40 from 0.117 inches to about 0.106 inches, while the distal portion 50 (e.g., about 25 cm) is maintained at 0.117 inches. Such modification produces a tubular member 40 having the features of the present embodiment.

It should be appreciated that, instead of reducing the outside diameter of a standard guiding catheter, the tubular member 40 could comprise two separate pieces having different diameters which are joined together using, for example, adhesive. Furthermore, the tubular member 40 could comprise materials other than a standard three-layer guiding catheter, such as hypodermic tubing lined with a low-friction polymer, or other appropriate tubing.

Figures 2B, 3:
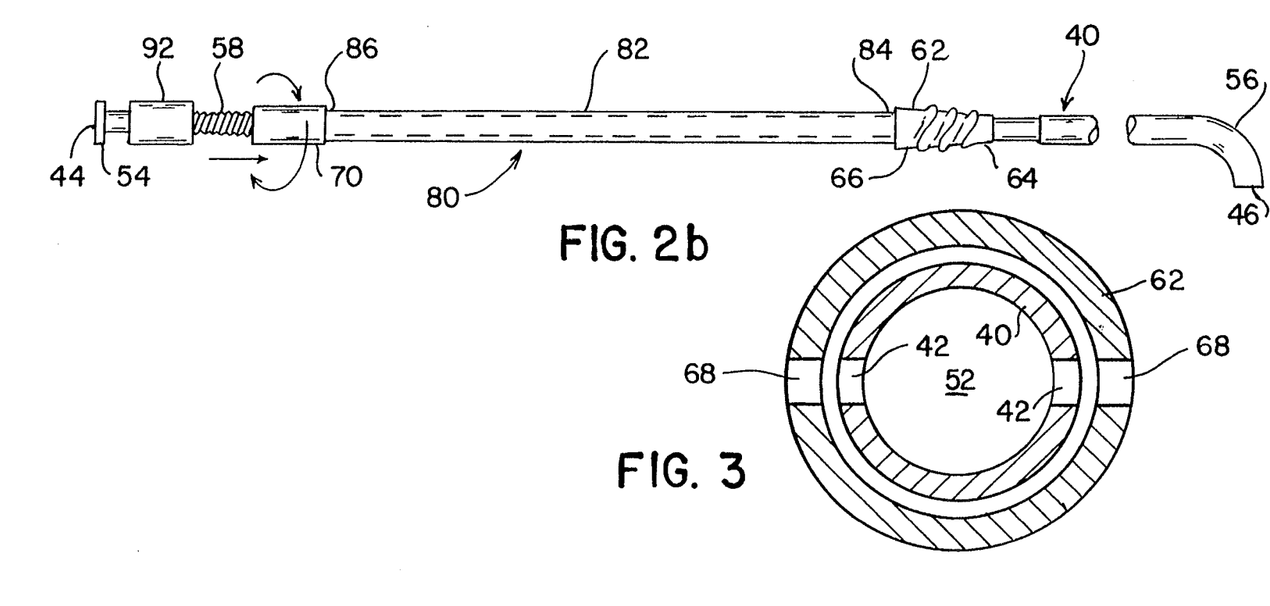

Referring to FIGS. 2–3, two perfusion ports 42, each having a diameter of about 1 millimeter, are provided in the sidewall of the tubular member 40 between the distal tip 46 and proximal end 44. Preferably, the ports are located between about 25 cm and about 80 cm from the distal tip 46 and, more preferably, they are located in the proximal portion 48 of the tubular member 40, approximately 30 cm from the distal tip 46. Such location positions the perfusion ports in the descending aorta when the distal tip is seated in the selected vascular ostium, thereby avoiding the need for the closure member 60 and actuating member 80 to travel through the aortic arch. The perfusion ports 42 are positioned on opposing sides of the tubular member 40 (i.e., 180° from each other) and are designed to allow entrance of blood into the lumen 52 of the tubular member 40 to perfuse the selected coronary artery 22 during coronary intervention procedures. It should be appreciated that the tubular member 40 could have one or more perfusion ports 42 in any number of different positioning patterns (e.g., circumferentially spaced and/or axially spaced). The proximal end 44 of the tubular member 40 is provided with a luer fitting 54 for attachment of appropriate syringes or other medical devices (not shown) for various medical procedures.

The tubular member 40 of the present embodiment includes a curved section 56 adjacent to the distal tip 46 of the tubular member 40. Such curved section 56 arcs approximately 90° such that the opening in the distal tip 46 faces in a direction which is approximately perpendicular to the length dimension of the tubular member 40. The curved section 56 facilitates positioning of the distal tip 46 in the selected coronary ostium 24. It should be appreciated that the curved section 56 may be formed as one of many curve configurations routinely used for variations in anatomy.

As noted above, the means for selectively closing the perfusion ports 42 in the present embodiment generally includes a closure member 60 and an actuating member 80 for facilitating actuation of the closure member 60. The closure member 60 of the present embodiment comprises a hollow cylindrical member 62 positioned about the proximal portion 48 of the tubular member 40 in alignment with the perfusion ports 42. The cylindrical member 62 is about 1 cm long and is dimensioned to be slidable relative to the tubular member 40. In the present embodiment, the cylindrical member 62 has an inner diameter of about 0.110 inches (i.e., compared to an outer diameter of 0.106 for the proximal portion 48 of the tubular member 40) and an outer diameter of about 0.116 inches.

The cylindrical member 62 is made from an elastomeric material such as that sold under the trademark C-FLEX, but other materials, such as latex, silicone, or other thermoplastic elastomer could also be used. The distal end 64 of the cylindrical member 62 is secured to the proximal portion 48 of the tubular member 40 at a location distal to the perfusion ports 42. Such securement can be accomplished utilizing an appropriate adhesive, such as cyanoacrylate.

The cylindrical member 62 further includes two perfusion holes 68 through the sidewall thereof in alignment with the perfusion ports 42 in the tubular member 40, as shown in FIGS. 2a and 3. Such alignment of the perfusion holes 68 with the perfusion ports 42 provides a pathway for passive blood perfusion through the tubular member 40 and, therefore, is termed the "open condition." The cylindrical member 62 is designed such that rotational and axial movement of the proximal end 66 of the cylindrical member 62 relative to the distal end 64 of the cylindrical member 62 (i.e., twisting of the cylindrical member 62) will cause the perfusion holes 68 to become misaligned with the perfusion ports 42, as shown in FIG. 2b, thereby placing the perfusion ports 42 in the "closed condition." Such closed condition inhibits passive blood perfusion through the tubular member 40. Effective sealing of the perfusion ports 42 is facilitated by a decrease in diameter of the cylindrical member 62 which accompanies the twisting motion.

It can be appreciated that, in use, the perfusion ports 42 are positioned within a blood vessel and, accordingly, the cylindrical member 62 will also be positioned within the same blood vessel. As such, access to the proximal end 66 of the cylindrical member 62 for purposes of twisting the cylindrical member 62 and closing the perfusion ports 42 can be compromised. In this regard, and as briefly noted above, an actuating member 80 is operatively connected to the closure member 60 for facilitating actuation of the closure member 60. The actuating member 80 of the present embodiment includes a cylindrically-shaped sleeve member 82 secured at a distal end 84 to the proximal end 66 of the cylindrical member 62. The sleeve member 82 extends proximally from the cylindrical member 62 toward the proximal end 44 of the tubular member 40 and, as such, provides a means whereby the closure member 60 (i.e., the cylindrical member 62) can be actuated by the user of the device at the proximal end 44 of the tubular member 40 (i.e., outside of the blood vessel).

The sleeve member 82 is designed to have an inner diameter slightly greater than the outer diameter of the proximal portion 48 of the tubular member 40 such that, when the sleeve member 82 is positioned over the proximal portion 48 of the tubular member 40, there is a slidable fit therebetween. For example, in the present embodiment, the inner diameter of the sleeve member 82 is about 0.109 inches (compared to an outer diameter of about 0.106 for the proximal portion 48 of the tubular member 40) and the outer diameter of the sleeve member 82 is about 0.113 inches.

The length of the sleeve member 82 must be sufficient to allow operative actuation of the closure member 60 from a location near the proximal end 44 of the tubular member 40. That is, the sleeve member 82 must reach from the proximal end 66 of the cylindrical member 62 to near the proximal end 44 of the tubular member 40. In this regard, the length of the sleeve member 82 will vary depending on the relative positioning of the cylindrical member 62 and the tubular member 40. In the present embodiment, the sleeve member 82 is about 70 cm long.

The sleeve member 82 of the present embodiment is further designed to transmit a torque from its proximal end 86 to its distal end 84 to provide the required twisting motion to the cylindrical member 62, as described above. In this regard, the sleeve member 82 of the present embodiment comprises a semi-rigid polymer material, and preferably comprises polyimide tubing. A hemostasis valve contained within a hub 90 is secured to the proximal end 86 of the sleeve member 82 in order to inhibit leakage of fluid (e.g., blood and/or contrast media) between the tubular member 40 and the sleeve member 82. The hub 90 also serves as a grip which the user of the device can readily hold to provide rotational and axial movement of the sleeve member 82 relative to the tubular member 40 to close the perfusion ports 42.

Because of the elastomeric properties of the cylindrical member 62 of the preferred embodiment, the cylindrical member 62 can be used to bias the catheter toward a particular condition (i.e., perfusion ports open or closed). Preferably, the components of the catheter 30 are assembled in such a manner that the catheter 30 is biased toward the open condition. That is, when the sleeve member 82 is not moved (i.e., not rotated or axially displaced) by the user of the catheter, the perfusion holes 68 are aligned with the perfusion ports 42, thereby placing the perfusion ports in the open condition, as shown in FIGS. 2a and 3. Such open condition allows passive perfusion of blood through the perfusion ports to perfuse the selected coronary artery 22. A bias toward the open condition is beneficial in that it frees the users hands while still providing passive perfusion of the selected coronary artery 22, thereby allowing the user of the device to perform other procedures such as preparing medical devices (e.g., balloon catheters, atherectomy instruments, etc.) for insertion into the guiding catheter.

Conversely, when the sleeve member 82 is rotated and axially displaced relative to the tubular member 40 to cause twisting to the proximal end 66 of the cylindrical member 62 relative to the distal end 64 of the cylindrical member 62 (e.g., by about 3–4 revolutions), the cylindrical member 62 will twist, causing the cylindrical member 62 to "wrap" around the tubular member 40. Such wrapping of the cylindrical member 62 results in the cylindrical member 62 constricting in diameter and length and causes the perfusion holes 68 in the cylindrical member 62 to become misaligned with the perfusion ports 42 in the tubular member 40. Such constriction and misalignment effectively seals the perfusion ports, thereby placing the perfusion ports 42 in the tubular member 40 in the "closed condition" to inhibit passive blood perfusion through the tubular member 40, as shown in FIG. 2b. It should be appreciated that the biasing of the catheter toward a particular condition could instead be provided by any other suitable means, such as a torsion spring. Furthermore, it should be appreciated that the device could also be unbiased or could be biased toward the closed condition to achieve other advantages.

In order to ensure optimum closure of the perfusion ports, the present invention further includes means for limiting movement of the actuating member 80 relative to the tubular member 40. In the described embodiment, such means for limiting movement includes the provision of internal, screw-type threads 88 on the interior surface of the hub 90 attached to the sleeve member 82 and external, screw-type threads 58 on the exterior surface of a hub 92 attached to the tubular member 40. Such interior and exterior threads 58,88 mate with each other such that the hub 90 secured to the sleeve member 82 is threaded over the hub 92 secured to the tubular member 40. The threads 58,88 are further provided with a stop member (not shown), such as a discontinuity in the threads, for limiting rotation of the sleeve member 82 relative to the tubular member 40. It should be appreciated that any suitable means for limiting movement, such as intersecting boss members or a peg within a slot, may be used to limit movement of the actuating member 80 relative to the tubular member 40.

It should be appreciated that the actuating member 80 and closure member 60 of the present invention could comprise a single member rather than two adhesively-connected pieces. For example, the means for closing the perfusion ports 42 could comprise a single cylindrical sheath slidably positioned about the tubular member 40 in a manner similar to the sleeve member 82 described above (i.e., proximal to the perfusion ports 42). Such sheath could be advanced or withdrawn axially relative to the tubular member 40 to selectively cover/uncover the perfusion ports 42. Furthermore, the means for closing could comprise a cylindrical sheath slidably positioned about the tubular member 40 such that at least a portion of the sheath is aligned with the perfusion ports 42 (i.e., the sheath covers the perfusion ports 42). Such sheath could include perfusion holes through a sidewall thereof which could be selectively aligned/misaligned with the perfusion ports 42 in the tubular member 40 (e.g., by rotating and/or axially displacing the sheath relative to the tubular member 40) to selectively open/close the perfusion ports 42. Such sheaths could also be positioned inside the tubular member 40, while still performing the required functions.

In operation, the guiding catheter 30 can be used to guide medical instruments to a selected blood vessel for intervention and/or diagnostic purposes. The catheter is typically introduced into the vascular system through a catheter introducer. The catheter is then advanced through the blood vessel until the distal tip is positioned at or near the ostium of the selected blood vessel. At this point, the perfusion ports can be advantageously closed by securing the tubular member relative to the blood vessel (e.g., by grasping the hub 92), grasping the actuating member (e.g., by grasping the hub 90), and rotating/axially displacing the actuating member relative to the tubular member to move the closure member from the first position to the second position. The position of the distal tip can then be detected by one or more techniques and the distal tip can be repositioned utilizing the information from the step of detecting the position of the distal tip. The steps of detecting the position of the distal tip and repositioning the distal tip can be iteratively performed until the distal tip is properly seated in the selected coronary ostium.

Figure 4:
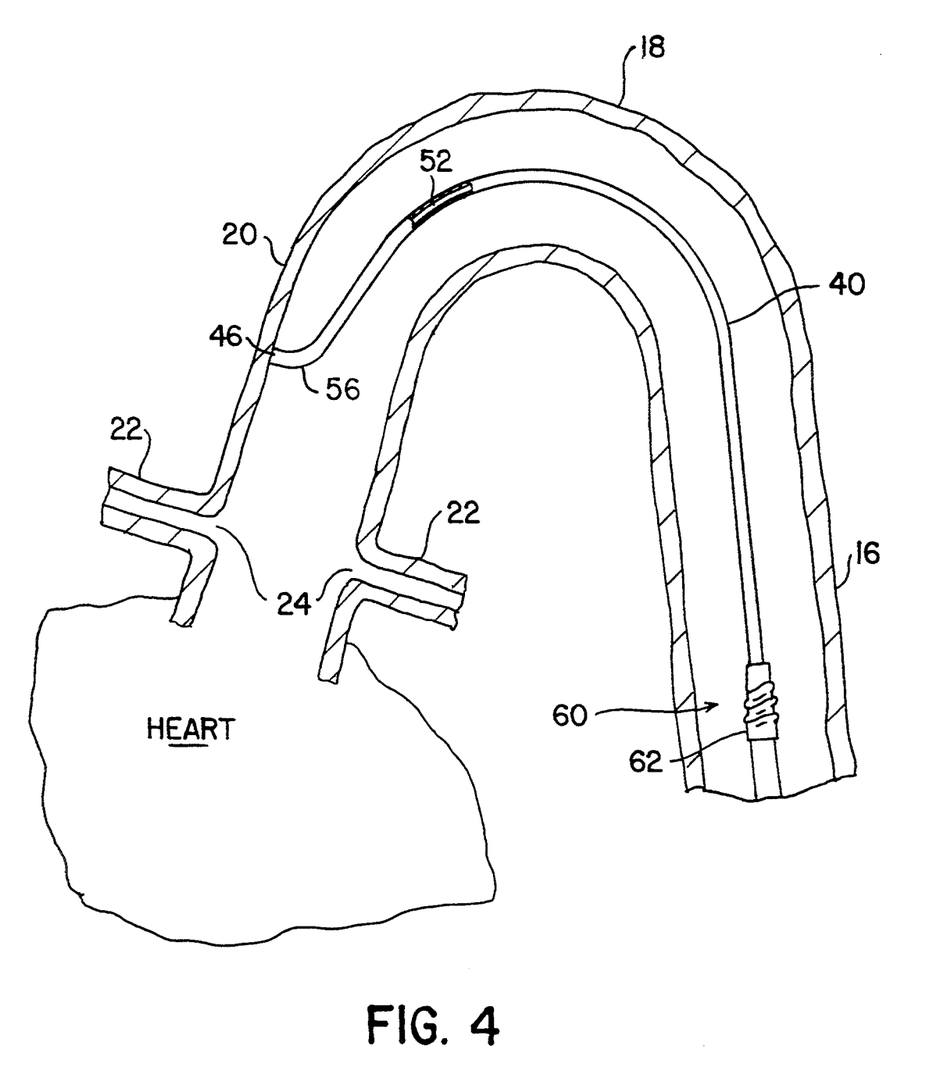
FIG. 4 is an exploded view of an aorta and coronary artery with a guiding catheter embodying the present invention improperly seated against an aortic wall.

The position of the distal tip may be detected by sensing the damping of the blood pressure wave which accompanies seating of the distal tip against the aortic wall. More specifically, with the distal tip 46 positioned in the ascending aorta 20, the blood pressure waves in the ascending aorta 20 will travel through the lumen 52 of the guiding catheter 30 (i.e., via the distal tip 46) and can be monitored by the user of the guiding catheter 30 utilizing standard pressure sensors (not shown) located at the proximal end 44 of the guiding catheter 30. With the perfusion ports 42 in the closed condition, if the distal tip 46 should become improperly seated against the aorta wall, as shown in FIG. 4, the blood pressure wave travelling through the lumen 52 of the guiding catheter 30 will become damped. Such damping of the blood pressure wave can be detected by the physician (e.g., utilizing standard pressure sensors at the proximal end 44 of the tubular member 40), thus indicating that the distal tip 46 is improperly seated. Utilizing such data, the distal tip can then be repositioned.

The position of the distal tip may also be detected by injecting contrast media through the tubular member and out the distal tip such that the position of the tubular member can be visualized utilizing an x-ray monitor (e.g., a fluoroscope). With the perfusion ports closed, substantially all of the contrast media will flow out the distal tip, rather than out the perfusion ports, thereby providing adequate visualization of the location of the distal tip. It should be appreciated that, without the provision of closeable perfusion ports, a substantial portion of the contrast media could exit the tubular member through the perfusion ports and, therefore, may not be advantageously directed near the distal tip. This is especially true if the perfusion ports are located a large distance from the distal tip such as, for example, in the descending aorta. The problem is compounded by the fact that, when the catheter is fed upstream (i.e., against the blood flow), the contrast media which exits through the perfusion ports in known devices flows away from the distal tip and is therefore effectively useless in detecting the position of the distal tip relative to the selected vascular ostium.

Figure 5:
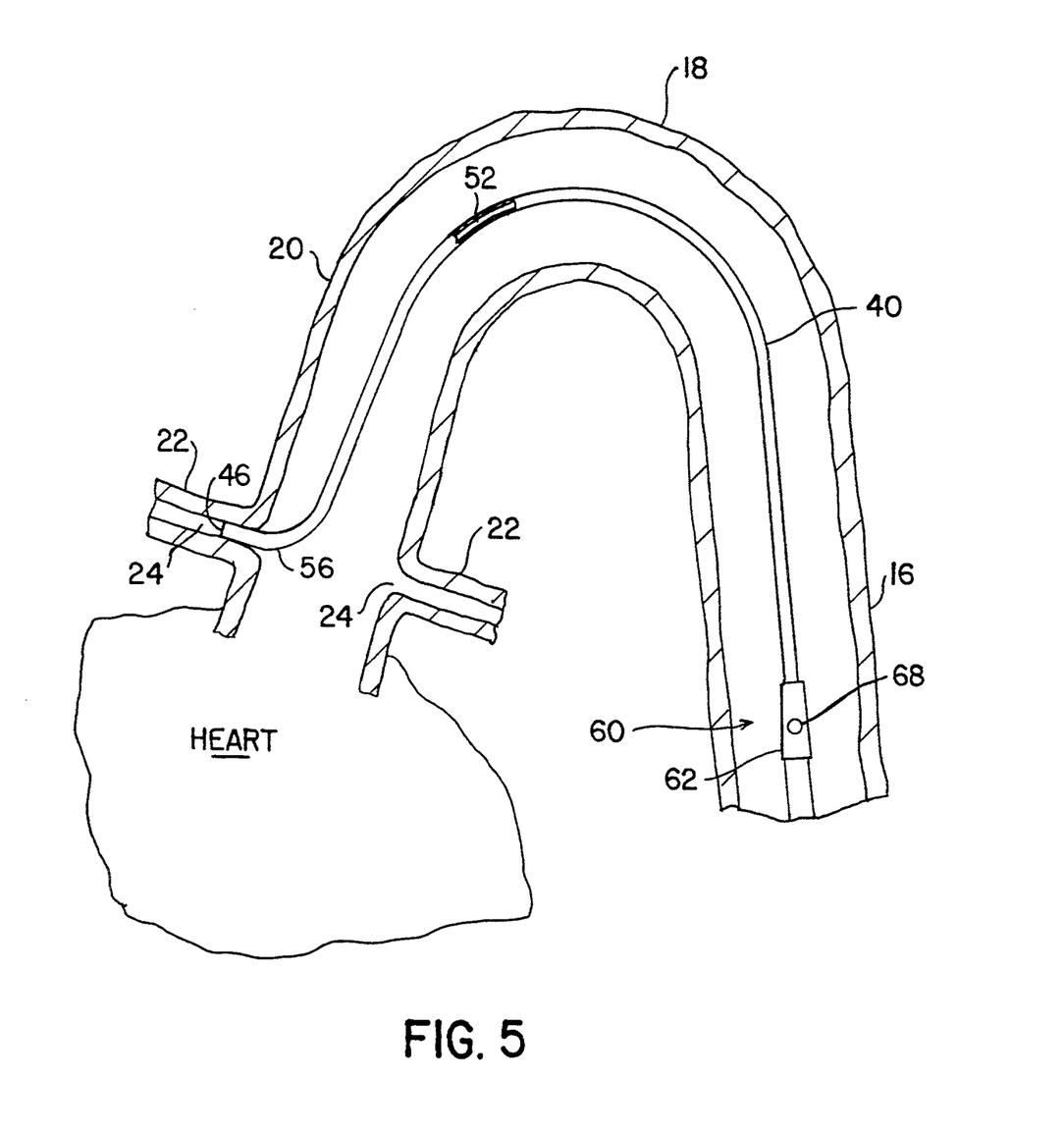
FIG. 5 is the exploded view of FIG. 3 with a guiding catheter embodying the present invention properly positioned to perform a coronary intervention procedure.

After the distal tip 46 has been properly seated, as shown in FIG. 5, the provision of controllable perfusion ports 42 can aid in the selective injection of contrast media into the coronary artery 22 (i.e., for purposes of visualizing the vascular lumen). When injecting contrast media into an artery, it is desirable to direct most, and preferably all, of the contrast media into the selected artery. In this regard, the illustrated guiding catheter can be used to visualize a blood vessel by a method comprising the steps of seating the distal tip in a selected vascular ostium (described above), at least partially closing the perfusion ports, and introducing contrast media into the tubular member after the perfusion ports have been closed. As noted above, the perfusion ports of the illustrated embodiment are closed by securing the tubular member relative to the blood vessel, grasping the actuating member, and rotating/axially displacing the actuating member relative to the tubular member to move the closure member from the first position to the second position. Such closed condition substantially prevents contrast media from exiting through the perfusion port and dispersing with blood flow in the aorta, thereby efficiently providing contrast media to the selected blood vessel. Furthermore, the concentration of contrast media being introduced into the selected artery is enhanced, thereby improving visualization of the vascular defect. Utilizing less contrast media further reduces the likelihood of complications (e.g., kidney failure or the like) associated with excessive contrast media injection.

The above method of selectively injecting contrast media into the coronary artery can further comprise the step of selectively perfusing the coronary artery. To perfuse the coronary artery, the perfusion ports may be selectively maintained in the open condition to allow blood to enter the tubular member (i.e., through the perfusion ports) and exit the tubular member through the distal tip to perfuse the coronary artery. Such perfusion of the coronary artery may be selectively allowed/inhibited by selectively opening/closing the perfusion ports, as described above.

It should be appreciated that, without the provision of closeable perfusion ports 42, the above-described methods cannot be performed. For example, without selectively closable perfusion ports, the blood pressure waves in the lumen of the catheter would not be significantly damped (i.e., because the blood pressure wave would still transmit to the lumen of the guiding catheter via the perfusion ports). Furthermore, without the ability to close the perfusion ports before injecting contrast media for purposes of detecting the position of the distal tip relative to the selected vascular ostium, at least a portion of the contrast media will exit through the perfusion ports, thereby wasting contrast media, compromising visualization of the distal tip, and potentially causing medical complications. Similarly, when injecting contrast media for purposes of visualizing a vascular lumen, the absence of selectively closable perfusion ports will result in at least a portion of the contrast media mixing with aortic blood, resulting in similar disadvantages. In addition, perfusion of the coronary artery would be compromised.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodi7 ments and with various modifications required by the particular applications or uses of the present invention. It is intended that the appended claims be construed to include alternative embodiments to the extent permitted by the prior art.

What is claimed is:

1. A guiding catheter, comprising:

an elongated tubular member open at both a proximal end and a distal tip and including at least one perfusion port in a sidewall thereof;

a closure member positioned adjacent said perfusion port and movable between at least first and second positions to open and close said perfusion port, said first position corresponding with said perfusion port being open and said second position corresponding with said perfusion port being closed wherein a substantially sealed pathway is defined between said distal tip and said proximal end of said tubular member when said perfusion port is closed; and an actuating member operatively connected to said closure member and extending proximally therefrom toward said proximal end of said tubular member, whereby said actuating member is selectively moveable to move said closure member between said first and second positions.

2. A guiding catheter, as set forth in claim 1, further comprising:

biasing means for biasing said cylindrical member toward one of said first and second positions.

3. A guiding catheter, as set forth in claim 1, further comprising:

means for limiting movement of said actuating member relative to said tubular member.

4. A guiding catheter, as set forth in claim 1, wherein said closure member includes a cylindrical member having a perfusion hole through a sidewall thereof, said perfusion hole being in alignment with said perfusion port when said closure member is in said first position and being misaligned with said perfusion port when said closure member is in said second position.

5. A guiding catheter, as set forth in claim 4, wherein a proximal end of said cylindrical member is secured to a distal end of said actuating member.

6. A guiding catheter, as set forth in claim 5, wherein said cylindrical member includes an elastomeric material and wherein a distal end of said cylindrical member is secured to said tubular member, whereby rotation of said actuating member relative to said tubular member will cause rotation of said proximal end of said cylindrical member relative to said distal end of said cylindrical member to thereby twist said cylindrical member.

7. A guiding catheter, as set forth in claim 4, wherein said tubular member includes a distal portion and a proximal portion, said distal portion having an outer diameter larger than an outer diameter of said proximal portion, and wherein said cylindrical member is positioned about said proximal portion of said tubular member.

8. A guiding catheter, as set forth in claim 1, wherein said actuating member includes a sleeve member slidably positioned adjacent said tubular member.

9. A guiding catheter, as set forth in claim 8, wherein said tubular member includes a distal portion and a proximal portion, said distal portion having an outer diameter larger than an outer diameter of said proximal portion, and wherein said sleeve member is positioned about said proximal portion of said tubular member.

10. A guiding catheter, as set forth in claim 8, wherein said sleeve member includes a hemostasis valve positioned on a proximal end thereof for providing a seal between said tubular member and said sleeve member.

11. A guiding catheter, as set forth in claim 1, wherein said actuating member is threadably interconnected with said tubular member.

12. A guiding catheter, as set forth in claim 1, wherein said perfusion port is located between about 15 cm and about 100 cm from said distal tip.

13. A guiding catheter for use in providing access to a coronary artery via an aorta, said guiding catheter comprising:

an elongated tubular member positionable in the aorta with an open distal tip positionable in a coronary ostium, said tubular member including at least one perfusion port in a sidewall thereof, whereby blood in the aorta is flowable into said perfusion port and through said tubular member and out said open distal tip to perfuse the coronary artery;

a cylindrical member positioned about said tubular member and having a distal end secured to said tubular member, said cylindrical member including a perfusion hole through a sidewall thereof, said perfusion hole being in alignment with said perfusion port when said cylindrical member is in a first position and being misaligned with said perfusion port when said cylindrical member is a second position; and a sleeve member movably positioned about said tubular member and secured to a proximal end of said cylindrical member, whereby said sleeve member is selectably rotatable relative to said tubular member to twist said cylindrical member between said first position and said second position.

14. A guiding catheter, as set forth in claim 13, further comprising:

biasing means for biasing said cylindrical member toward one of said first and second positions.

15. A guiding catheter, as set forth in claim 13, wherein said cylindrical member comprises an elastomeric material.

16. A guiding catheter, as set forth in claim 13, wherein said tubular member includes a distal portion and a proximal portion, said distal portion having an outer diameter larger than an outer diameter of said proximal portion, and wherein said cylindrical member and said sleeve member are positioned about said proximal portion of said tubular member.

17. A guiding catheter, as set forth in claim 13, wherein said sleeve member includes a hemostasis valve positioned on a proximal end thereof for providing a seal between said tubular member and said sleeve member.

18. A guiding catheter, as set forth in claim 13, wherein said perfusion port is located between about 15 cm and about 100 cm from said distal tip.

19. A method for use in seating a guiding catheter in a selected vascular ostium of a patient, the guiding catheter including an elongated tubular member open at a distal tip and including at least one perfusion port in a sidewall thereof, and means for selectively opening and closing the perfusion port, said method comprising the steps of:

introducing the guiding catheter into a blood vessel;

advancing the guiding catheter through the blood vessel toward the selected vascular ostium;

detecting a position of the distal tip relative to the selected vascular ostium while the perfusion port is at least partially closed; and selectively perfusing a blood vessel.

20. A method, as set forth in claim 19, further comprising:

positioning the distal tip relative to the selected vascular ostium utilizing an output from said step of detecting a position of the distal tip.

21. A method, as set forth in claim 19, wherein said step of selectively perfusing comprises:
selectively opening the perfusion port.

22. A method, as set forth in claim 21, wherein the means for selectively opening and closing the perfusion port includes a closure member positioned adjacent the perfusion port, and wherein said step of selectively opening the perfusion port comprises:
selectively moving the closure member relative to the perfusion port.

23. A method, as set forth in claim 22, wherein said step of selectively moving the closure member comprises:
rotating the closure member relative to the perfusion ports.

24. A method, as set forth in claim 22, wherein said step of moving the closure member comprises:
axially displacing the closure member relative to the perfusion ports.

25. A method, as set forth in claim 22, wherein the means for selectively opening and closing the perfusion port further includes an actuating member operatively connected to the closure member, wherein the closure member is movable relative to the perfusion port from a first position, where the perfusion port is open, to a second position, where the perfusion port is at least partially closed, and wherein said step of selectively moving the closure member comprises:
securing the tubular member relative to the blood vessel; and
moving the actuating member relative to the tubular member to move the closure member from the second position to the first position.

26. A method, as set forth in claim 25, wherein the closure member comprises an elastomeric cylindrical member secured at one end to the tubular member and secured at another end to the actuating member, and wherein said step of moving the actuating member comprises:
rotating and axially displacing the actuating member relative to the tubular member.

27. A method, as set forth in claim 19, wherein the means for selectively opening and closing the perfusion port is biased toward an open condition, and wherein said method further comprises, before said detecting step, the step of:
selectively at least partially closing the perfusion port to inhibit blood flow through the guiding catheter.

28. A method, as set forth in claim 19, wherein said step of detecting a position of the distal tip comprises:
sensing a blood pressure wave in the tubular member.

29. A method, as set forth in claim 19, wherein said step of detecting a position of the distal tip comprises:
injecting contrast media through the tubular member with the perfusion port at least partially closed; and
viewing the position of the distal tip relative to the selected vascular ostium utilizing an x-ray monitor.

30. A method, as set forth in claim 20, wherein said step of detecting a position of the distal tip and said step of positioning the distal tip are iteratively performed until the distal tip is seated in the selected vascular ostium.

31. A method, as set forth in claim 20, wherein said step of positioning the distal tip is selected from the group consisting of: advancing the distal tip; withdrawing the distal tip; and rotating the distal tip.

32. A method for use in visualizing a blood vessel lumen of a patient using a guiding catheter, the guiding catheter including an elongated tubular member open at a distal tip and including at least one perfusion port in a sidewall thereof, and means for selectively opening and closing the perfusion port, said method comprising the steps of:
seating the distal tip in a vascular ostium; and
introducing contrast media into the guiding catheter and blood vessel lumen with the perfusion port at least partially closed; and
selectively perfusing the selected blood vessel.

33. A method, as set forth in claim 32, wherein said step of perfusing comprises:
selectively opening the perfusion port.

34. A method, as set forth in claim 33, wherein the means for selectively opening and closing the perfusion port includes a closure member positioned adjacent the perfusion port, and wherein said step of opening the perfusion port comprises:
selectively moving the closure member relative to the perfusion port.

35. A method, as set forth in claim 34, wherein said step of moving the closure member comprises:
rotating the closure member relative to the perfusion ports.

36. A method, as set forth in claim 34, wherein said step of moving the closure member comprises:
axially displacing the closure member relative to the perfusion ports.

37. A method, as set forth in claim 34, wherein the means for selectively opening and closing the perfusion port further includes an actuating member operatively connected to the closure member, wherein the closure member is movable relative to the perfusion port from a first position, where the perfusion port is open, to a second position, where the perfusion port is at least partially closed, and wherein said step of selectively moving the closure member comprises:
securing the tubular member relative to the blood vessel; and
moving the actuating member relative to the tubular member to move the closure member from the second position to the first position.

38. A method, as set forth in claim 37, wherein the closure member comprises an elastomeric cylindrical member secured at one end to the tubular member and secured at another end to the actuating member, and wherein said step of moving the actuating member comprises:
rotating and axially displacing the actuating member relative to the tubular member.

39. A method, as set forth in claim 32, wherein the means for selectively opening and closing the perfusion port is biased toward an open condition, and wherein said method further comprises, before said introducing step, the step of:
selectively at least partially closing the perfusion port to inhibit blood flow through the guiding catheter.

40. A method for use in introducing a material into living tissue using a guiding catheter, the guiding catheter including an elongated tubular member open at a distal tip and including at least one side port in a sidewall thereof, and means for selectively opening and closing the side port, said method comprising the steps of:

positioning the distal tip within the living tissue;

introducing a material through the tubular member and into the living tissue with the side port at least partially closed; and selectively opening the side port.

41. A guiding catheter, comprising:

an elongated tubular member open at both a proximal end and a distal tip and including at least one perfusion port in a sidewall thereof;

a closure member positioned adjacent to said perfusion port and movable between at least first and second positions to open and close said perfusion port, said first position corresponding with said perfusion port being open and said second position corresponding with said perfusion port being closed;

an actuating member operatively connected to said closure member and extending proximally therefrom toward said proximal end of said tubular member, whereby said actuating member is selectively movable to move said closure member between said first and second positions; and biasing means for biasing said closure member toward one of said first and second positions.

42. A guiding catheter, comprising:

an elongated tubular member open at both a proximal end and a distal tip and including at least one perfusion port in a sidewall thereof, said tubular member including a distal end having a generally arcuate configuration;

a closure member positioned adjacent to said perfusion port and movable between at least first and second positions to open and close said perfusion port, said first position corresponding with said perfusion port being open and said second position corresponding with said perfusion port being closed; and an actuating member operatively connected to said closure member and extending proximally therefrom toward said proximal end of said tubular member, whereby said actuating member is selectively movable to move said closure member between said first and second positions.

43. A guiding catheter, comprising:

an elongated tubular member open at both a proximal end and a distal tip and including at least one perfusion port in a sidewall thereof, said perfusion port being positioned between about 15 cm and about 100 cm from said distal tip;

a closure member positioned adjacent to said perfusion port and movable between at least first and second positions to open and close said perfusion port, said first position corresponding with said perfusion port being open and said second position corresponding with said perfusion port being closed; and an actuating member operatively connected to said closure member and extending proximally therefrom toward said proximal end of said tubular member, whereby said actuating member is selectively movable to move said closure member between said first and second positions.

* * * * *